United States Patent [19]

Essig et al.

[11] Patent Number: 5,645,083

[45] Date of Patent: *Jul. 8, 1997

[54] PERITONEAL SURGICAL METHOD

[76] Inventors: Mitchell N. Essig, 227 High Brook Ct., Pelham, N.Y. 10803; Peter J. Wilk, 185 West End Ave., New York, N.Y. 10023

[*] Notice: The term of this patent shall not extend beyond the expiration date of Pat. No. 5,279,548.

[21] Appl. No.: 195,930

[22] Filed: Feb. 10, 1994

[51] Int. Cl.⁶ .................................................. A61M 1/00
[52] U.S. Cl. .............................. 128/898; 604/27; 606/108
[58] Field of Search ................... 128/897–98, DIG. 24; 606/108, 110, 114, 127; 604/27–46, 55, 96

[56] References Cited

U.S. PATENT DOCUMENTS

| | | |
|---|---|---|
| 30,471 | 10/1860 | Dudley . |
| 3,472,230 | 10/1969 | Fogarty . |
| 3,794,044 | 2/1974 | Vennard et al. . |
| 3,882,852 | 5/1975 | Sinnreich . |
| 4,990,151 | 2/1991 | Wallstén . |
| 5,011,488 | 4/1991 | Ginsburg . |
| 5,037,379 | 8/1991 | Clayman et al. ................ 128/DIG. 24 |
| 5,176,687 | 1/1993 | Hasson et al. . |
| 5,190,555 | 3/1993 | Wetter et al. . |
| 5,190,561 | 3/1993 | Graber . |
| 5,192,284 | 3/1993 | Pleatman . |
| 5,209,754 | 5/1993 | Ahluwalia . |
| 5,215,521 | 6/1993 | Cochran et al. ................ 128/DIG. 24 |
| 5,217,466 | 6/1993 | Hasson . |
| 5,234,439 | 8/1993 | Wilk et al. ................ 606/110 |
| 5,279,539 | 1/1994 | Bohan et al. ................ 606/110 |
| 5,279,548 | 1/1994 | Essig et al. ................ 606/108 |
| 5,352,184 | 10/1994 | Goldberg et al. ................ 128/DIG. 24 |
| 5,374,273 | 12/1994 | Nakao et al. ................ 128/898 |

FOREIGN PATENT DOCUMENTS 2739589  3/1979  Germany .

*Primary Examiner*—Lee S. Cohen
*Assistant Examiner*—John P. Lacyk
*Attorney, Agent, or Firm*—McAulay Fisher Nissen Goldberg & Kiel, LLP

[57] ABSTRACT

In a pelvic or peritoneal surgical method, a funnel shaped membrane is inserted in a closed configuration through a laparoscopic trocar sleeve into the abdominal cavity of a patient. The membrane is spread from the closed configuration to an opened configuration upon emergence of the membrane into the abdominal cavity. The opened membrane and an internal organ of the patient are then positioned relative to one another so that the organ is disposed essentially vertically above the opened membrane. Upon proper positioning, the organ is subjected to a laparoscopic surgical operation while the organ is disposed above the opened membrane, whereby tissue particles and fluid escaping the organ during the operation fall into the opened membrane. The membrane and collected tissue particles and fluid are removed from the abdominal cavity upon termination of the operation.

20 Claims, 3 Drawing Sheets

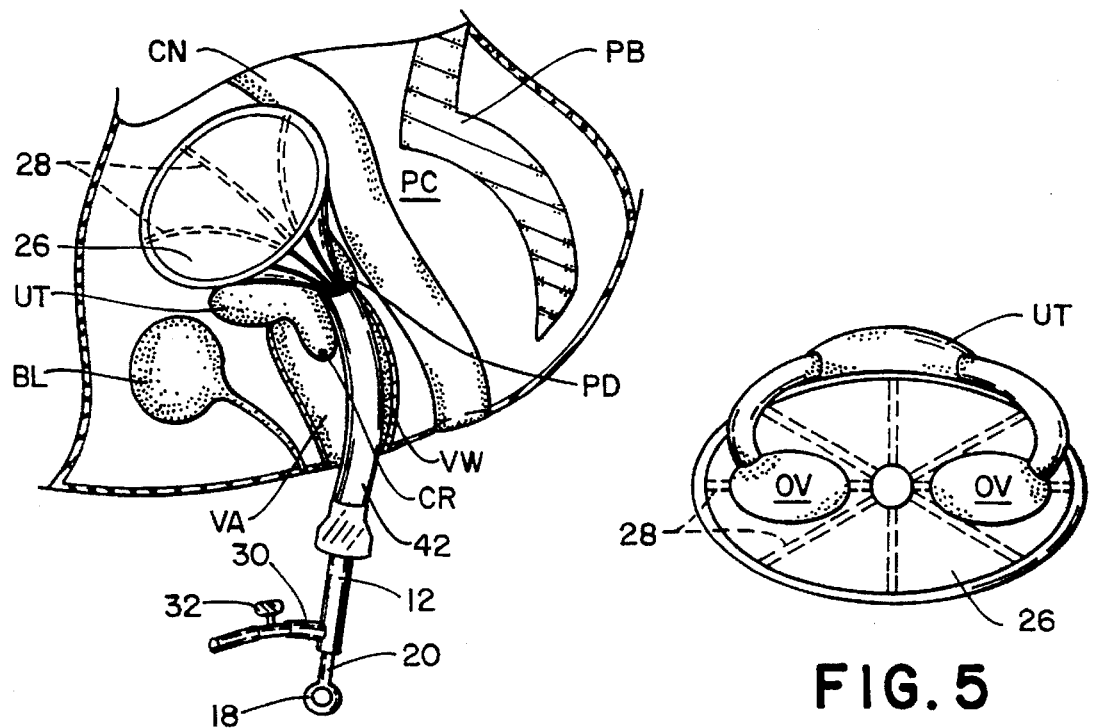
FIG. 4
FIG. 5
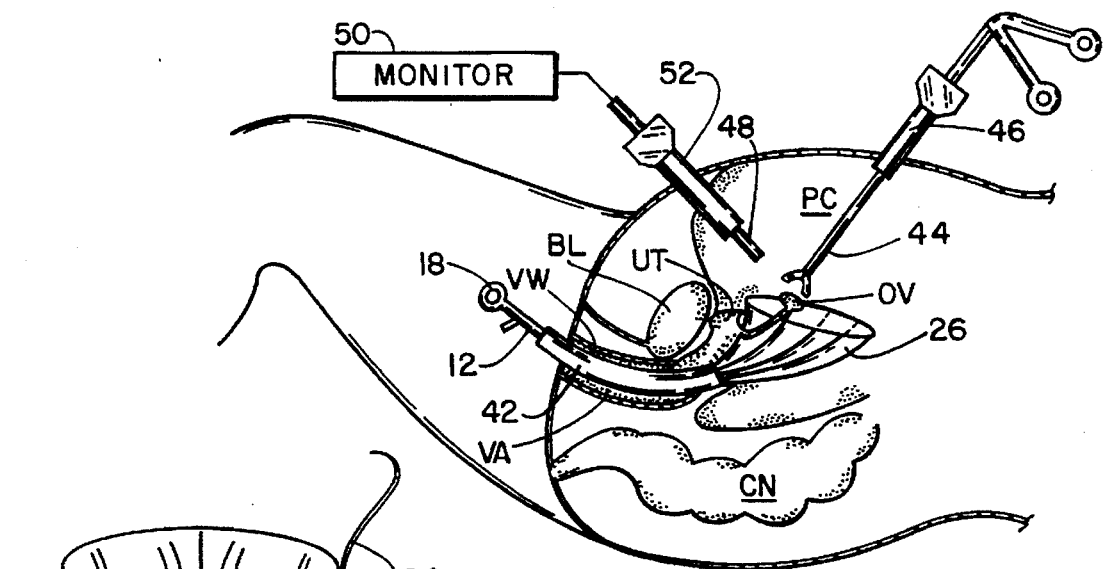
FIG. 6
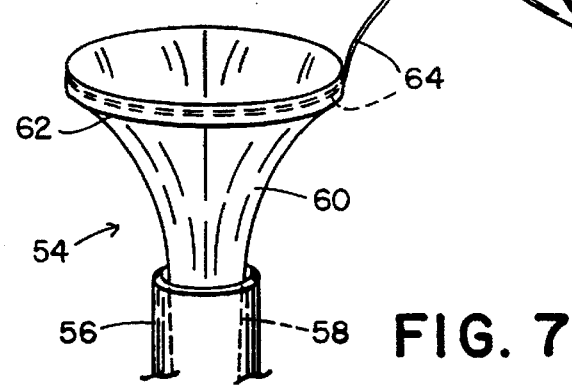
FIG. 7

PERITONEAL SURGICAL METHOD

BACKGROUND OF THE INVENTION

This invention relates to a method for use in performing surgery in the peritoneal cavity. The method is particularly useful in laparoscopic operations on an ovary.

Ovarian cysts, particularly in women over the age of 45, are sometimes malignant. In a surgical operation to remove such a cyst, it is imperative to avoid having fluids drip from the cyst onto underlying normal tissues. If the fluid leaks and touches peritoneal surfaces, there is a danger that the malignancy may spread.

Operations on the female organs are frequently performed laparoscopically. Laparoscopic surgery involves the insufflation of the abdominal cavity with carbon dioxide and the placement of cannulas in the abdominal wall of the patient. Distal end portions of laparoscopic instruments are inserted through the cannulas for performing an operation inside the abdominal cavity by surgeons manipulating the proximal ends of the instruments. Laparoscopic instruments include a fiber-optic laparoscope which enables visual monitoring of abdominal organs, as well as the distal end portions of the operating instruments.

Performing an operation laparoscopically, instead of via a traditional open incision, provides the substantial benefits of reducing patient trauma and hospital convalescent time. However, in laparoscopic surgery to remove an ovarian cyst, there is always leakage from the cyst, with the attendant risk that the cyst may be malignant and that the malignancy may spread to underlying peritoneal tissues.

OBJECTS OF THE INVENTION

An object of the present invention is to provide a method for use in peritoneal surgery.

Another object of the present invention is to provide such a method which is particularly useful in preventing organic debris from a surgical site from falling on underlying tissues of the patient.

Another, more particular, object of the present invention is to provide such a method which is used in laparoscopic surgery.

A further particular object of the present invention is to provide a method which can be used to remove organic debris including fluids, particulate matter and organic masses from a patient's peritoneal cavity during and at the end of a peritoneal operation, whether of the open incision or the laparoscopic variety.

Yet another particular object of the present invention is to provide such a method which substantially minimizes trauma to the patient and reduces healing time.

These and other objects of the present invention will be apparent from the drawings and detailed descriptions herein.

SUMMARY OF THE INVENTION

A method for use in pelvic or peritoneal surgery comprises, in accordance with the present invention, the steps of (a) providing a trocar sleeve and a funnel shaped membrane, (b) positioning the sleeve in the abdominal wall of the patient so that a distal end portion of the sleeve extends into the abdominal cavity, (c) inserting the membrane in a closed configuration through the sleeve into the abdominal cavity of the patient, (d) spreading the membrane from the closed configuration to an opened configuration upon emergence of the membrane into the abdominal cavity, (e) positioning the opened membrane and an internal organ of the patient relative to one another so that the organ is disposed essentially vertically above the opened membrane, (f) operating on the organ while the organ is disposed above the opened membrane, whereby tissue particles and fluid escaping the organ during the operation fall into the opened membrane, and (g) removing the membrane and collected tissue particles and fluid from the abdominal cavity upon termination of the operation.

According to another feature of the present invention, the removal of the membrane and collected tissue particles and fluid includes the steps of (i) providing a laparoscopic suction instrument, (ii) inserting a distal end portion of the suction instrument into the abdominal cavity of the patient, and (iii) operating the suction instrument to suck collected tissue particles and fluid from the opened membrane.

Where the membrane has a mouth and a tapered side opposite the mouth, the step of removing the membrane further includes the step of drawing the membrane, the tapered side first, through a perforation in the abdominal wall of the patient. The perforation may be the same perforation which was traversed by the trocar sleeve. In that event, the membrane may be removed through the trocar sleeve or may be pulled through the perforation subsequently to the removal of the trocar sleeve from the abdominal wall.

According to a more particular feature of the present invention, the removal of the membrane entails the step of closing the mouth of the membrane prior to the drawing of the membrane through the perforation in the patient's abdominal wall. The closing of the membrane may be implemented by drawing closed a purse string about the mouth of the membrane.

According to an additional feature of the present invention, the method comprises the steps of dropping a large mass of organic tissues into the opened membrane during the surgical operation, closing the membrane about the tissue mass, and withdrawing the mass with the sleeve through the vaginal wall of the patient. Again, the closing of the membrane may be implemented by drawing closed a purse string about a mouth of the membrane.

The spreading of the membrane may be accomplished automatically, for example, by attaching elongate spring members to the membrane. The spring members extend longitudinally, are spaced from one another about the membrane, and are biased to spread the membrane to an opened, funnel-like configuration. Alternatively, an oval or circular spring member may be attached to the mouth of the membrane, the spring member having a memory so as to return to an oval or circular configuration upon the relaxation of externally applied forces.

In a laparoscopic operation, a distal end portion of at least one laparoscopic operating instrument is inserted into the peritoneal cavity through an additional trocar sleeve positioned in an abdominal wall of the patient. The laparoscopic operating instrument is used, for example, to excise an ovarian cyst.

In a pelvic or peritoneal operation on a female patient utilizing a procedure in accordance with the present invention, virtually all organic by-products or debris of the operation on internal organs are caught and removed via the funnel membrane inserted through the pouch of Douglas. The risk of a malignancy spreading because of leaking fluid or dropped tissue parts is dramatically reduced, if not entirely eliminated.

A method in accordance with the present invention is particularly useful in laparoscopic surgery. Because the catcher funnel is inserted through the vaginal wall, the pain experienced by the patient is lessened. Recovery is accelerated because no muscles are involved and convalescent time is concomitantly reduced.

BRIEF DESCRIPTION OF THE DRAWING

FIG. 4 is a schematic cross-sectional view similar to FIG. 3, showing a step in a laparoscopic operation utilizing the instrument of FIG. 1 or 2.

FIG. 5 is a schematic top view of ovaries positioned over an opened funnel device during a method in accordance with the present invention.

FIG. 6 is a schematic cross-sectional view similar to FIG. 4, showing another step in a laparoscopic pelvic operation.

FIG. 7 is a schematic partial perspective view of another surgical funnel or catcher device for use in a laparoscopic pelvic operation.

DETAILED DESCRIPTION

Figure 1:
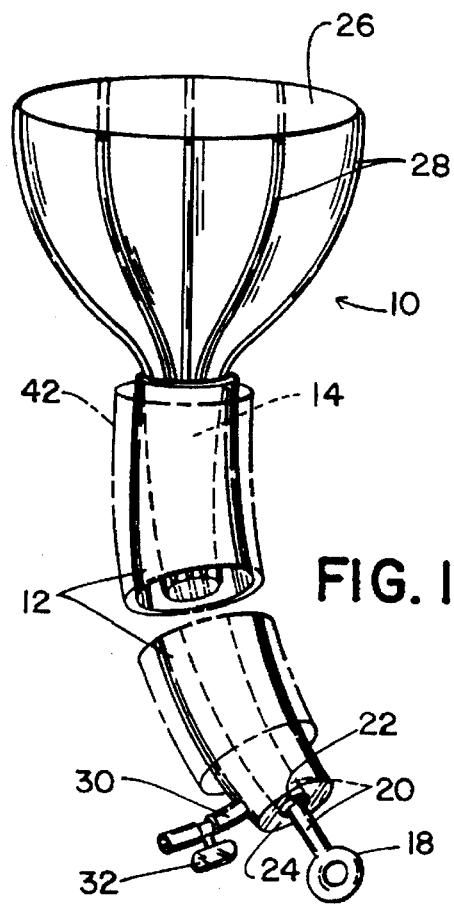
FIG. 1 is a schematic side perspective view of a surgical funnel or catcher device for use in a laparoscopic operation.

As illustrated in FIG. 1, a laparoscopic surgical instrument 10 comprises a flexible outer tubular member 12 in which a flexible inner tubular member 14 is slidably inserted. Inner tubular member 14 is provided at a proximal end with a handle or actuator 18 which is connected to the inner tubular member via a flexible rod 20. Rod 20 traverses an annular seal 22 provided in an end wall 24 in outer tubular member 12.

Inner tubular member 14 is provided at a distal end with an attached membrane 26 which is in a closed or collapsed storage configuration (not shown) when rod 20 is pulled to a proximal position and which assumes an opened funnel-shaped configuration upon a sliding of rod member 20 in a distal direction to eject the membrane from outer tubular member 12. Membrane 26 is supported in the opened or spread configuration by a plurality of elongate longitudinally extending spring elements or ribs 28 spaced from one another about the membrane. Ribs 28 have an internal spring bias tending to arc the ribs outwardly in the absence of closure forces such as those exerted by outer tubular member 12 when membrane 26 is pulled by rod 20 and tubular member 14 in a proximal direction. Ribs 28 may be connected at their proximal ends to the distal end of inner tubular member 14.

Inner tubular member 14 opens at a proximal end into outer tubular member 12 so as to enable a drainage of captured fluid from the inner tubular member to the outer tubular member. At a proximal or lower end, outer tubular member 12 is provided with an outlet port 30 in turn provided with a valve 32 for controlling the release of fluid from outer tubular member 12. Valve 32 is necessary to limit the loss of pneumoperitoneum during a laparoscopic surgical procedure (see FIG. 6).

Figure 2:
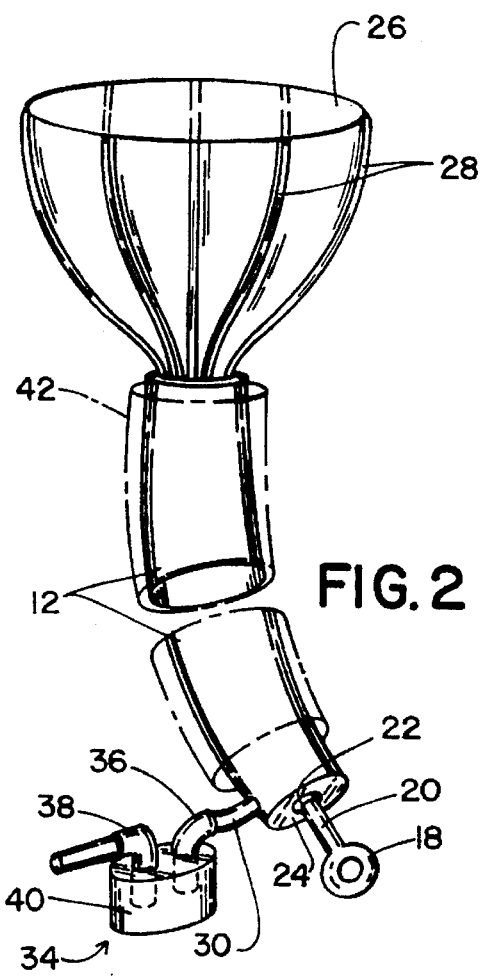
FIG. 2 is a schematic side perspective view of a surgical funnel device similar to that shown in FIG. 1, also for use in laparoscopic operation.

The laparoscopic instrument of FIG. 2 includes all of the elements of the laparoscopic surgical instrument 10 of FIG. 1, with the exception of valve 32. Instead of valve 32, a suction trap 34 is provided. Suction trap 34 includes an input tube 36, an output tube 38 and a specimen collecting container 40. A valve (not shown) may also be provided in either the input tube 36 or the output tube 38 to for controlling the loss of pneumoperitoneum.

Other modifications (not shown) may be made to the instrument assemblies of FIGS. 1 and 2. For example, inner tubular member 14 may extend through end wall 24 of outer tubular member 12, with outlet port 30 being connected to the inner tubular member rather than the outer tubular member. In that event, organic fluids from the patient are not leaked into the outer tubular member at all.

Inner tubular member 14 may be sufficiently thin to prevent the passage of any tissue segments of significant size. Alternatively or additionally, a screen or filter (not shown) may be provided at the upper or distal end of inner tubular member 14.

Outer tubular member 12 is insertable through a curved trocar sleeve 42 during a surgical procedure as described hereinafter with reference to FIGS. 4–6.

Figure 3:
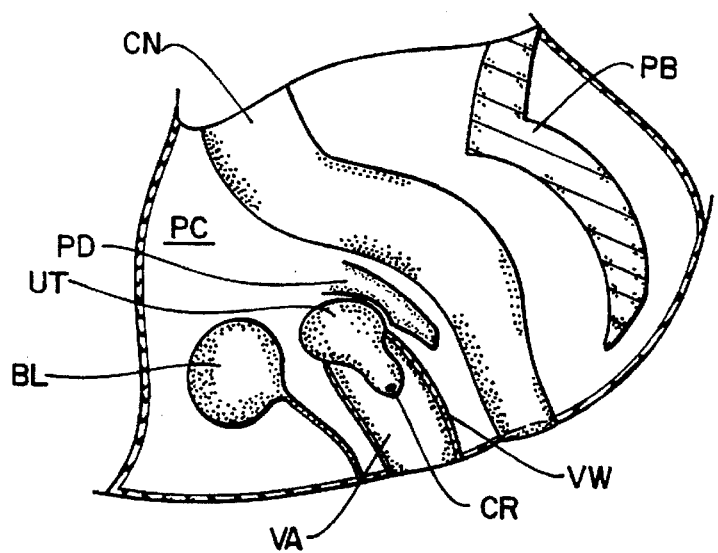
FIG. 3 is a diagram of selected parts of the female anatomy in the pelvic region.

As illustrated in FIG. 3, the female anatomy in the pelvic region includes a bladder BL, a uterus UT with a cervix CR, a vagina VA having a wall VW, a colon CN and a pelvic bone PB. In a region to the rear (to the right) of cervix CR, vagina wall VW is justaposed to a cul-de-sac in the peritoneal cavity PC which is known as the pouch of Douglas PD.

During an initial stage in a laparoscopic operation on an ovary OV (FIGS. 5 and 6), trocar sleeve 42 is inserted through vagina VA so that a distal portion of the sleeve traverses the vaginal wall VW and is partially disposed in the pouch of Douglas 42. The sleeve is so disposed in the usual manner with the aid of a trocar (not shown). Sleeve 42 is curved, as shown in FIG. 4, to facilitate vaginal penetration where the patient legs are in stirrups and the back is angled upwardly with respect to the horizontal.

Upon a withdrawal of the trocar from sleeve 42, instrument assembly 10 (or a modification thereof) with membrane 26 in a collapsed configuration inside tubular member 12 is inserted through sleeve 42 so that a distal end of tubular member 12 is roughly coterminal with the distal end of sleeve 42. Tubular member 12 may project beyond the distal end of sleeve 42, or may be inside the trocar sleeve.

Upon the desired positioning of outer tubular member 12 relative to trocar sleeve 42, handle 18 is used to push rod 20 and accordingly membrane 26 in the distal direction out from tubular member 12 and into the pouch of Douglas PD. Upon the emergence of membrane 26 from tubular member 12 and trocar sleeve 42, the membrane is spread out, under the action of ribs 28, to the opened configuration in the peritoneal cavity PC of the patient, as depicted in FIG. 4. A laparoscopic forceps 44 (FIG. 6) or other instrument may be used to position the opened membrane 26 in the peritoneal cavity PC. In addition, the laparoscopic forceps 44 and other instruments may be used to position a selected organ of the patient into position over the opened membrane 26. FIG. 5 shows ovaries OV positioned over the opened membrane in preparation for a laparoscopic operation on the ovaries.

As depicted in FIG. 6, a distal end portion of laparoscopic forceps 44 is inserted into the patient's peritoneal or abdominal cavity PC via a trocar sleeve 46 positioned in the abdominal walk AW. A laparoscope 48 operatively connected to a video monitor 50 is inserted through another trocar sleeve 52. During an operation on ovaries OV, tissue particles and fluid escaping the organs fall into opened membrane 26. The fluid and smaller particles are funneled through tubular member 14 to outlet 30 where they are collected for testing.

Larger tissue parts fall or drop into opened membrane 26 and remain therein until the end of the operation. At that time, inner tubular member 14 is withdrawn into outer tubular member 12, thereby forcing ribs 28 to fold towards one another in opposition to their own internal memory and concomitantly collapsing membrane 26 upon the captured tissue parts. With membrane 26 disposed partially outside tubular member 12, the entire assembly including trocar sleeve 42 and instrument assembly 10 may be withdrawn from the peritoneal cavity PC through the pouch of Douglas PD, vaginal wall VW and the vagina VA. The captured tissue parts are thus removed from the patient without touching the patient. A purse string (not shown) may be provided about the distal edge of membrane 26 to facilitate and ensure the closure therof about captured tissue parts. The string may extend back through trocar sleeve 42, whereby closure may be effectuated by pulling the string with one's hand. Alternatively, a forceps 44 may be used to close the purse string inside the abdominal cavity.

As illustrated in FIG. 7, a laparoscopic surgical instrument 54 comprises a flexible outer tubular member 56 in which a flexible inner tubular member 58 is slidably inserted. Inner tubular member 58 is provided at a distal end with an attached membrane 60. Upon an ejection of membrane 60 from the distal end of outer tubular member 56, the membrane 60 spreads out to an opened configuration under the action of an annular spring member 62 which defines a mouth 64 of the membrane. In order to collapse spring member 62 and concomitantly membrane 60 at the end of a laparoscopic surgical procedure, a purse-string-type closure device 64 is actuated by pulling on the purse string with a laparoscopic grasping forceps (not shown).

Figure 8:
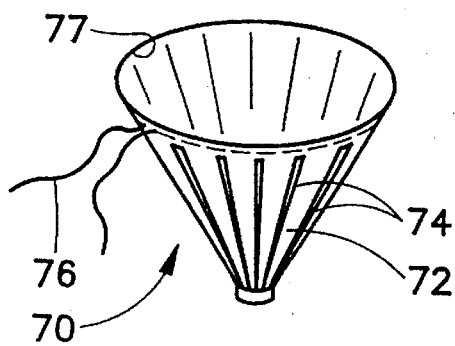
FIG. 8 is a schematic perspective view of a surgical funnel or catcher device for use in a laparoscopic operation in accordance with the present invention.

As illustrated in FIG. 8, a surgical catching device 70 includes a funnel shaped membrane 72 provided with a plurality of elongate ribs 74 having a memory or a spring bias tending to form the membrane into the opened configuration shown in FIG. 8. A purse string 76 may be provided at a mouth 77 of membrane 72 for closing the catcher device upon completion of a laparoscopic operation utilizing the device (see FIGS. 9A–9D). Ribs 74 cause membrane 72 to spread essentially automatically to the opened configuration upon a relaxation of any external stresses or forces placed upon the catching device.

Figure 9A:
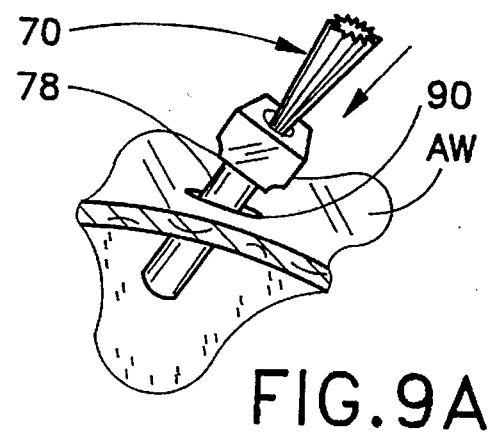
FIGS. 9A–9D are partially cross-sectional or broken-away views of a patient's abdomen during a laparoscopic operation, showing a method utilizing the device of FIG. 8, in accordance with the present invention.

As depicted in FIG. 9A, device 70 is inserted in a collapsed or closed configuration through a laparoscopic trocar sleeve 78 positioned in an abdominal wall AW of a patient. Catching device 70 may be sold in a sterilizing state and disposed inside an auxiliary sleeve (not shown) for transport prior to use. The auxiliary sleeve may be provided with a plunger (not shown) for pushing catching device 70 in the collapsed storage configuration from the auxiliary sleeve into trocar sleeve 78.

Figure 9B:
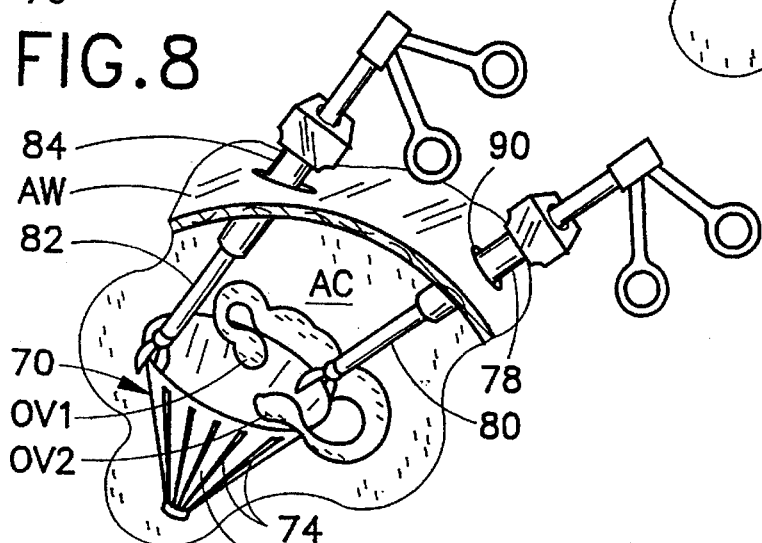

Upon insertion of catching device 70 through trocar sleeve 78 into an abdominal or peritoneal cavity AC of the patient, web or membrane 72 automatically opens under the action of ribs 74. At that juncture, laparoscopic grasping instruments 80 and 82 inserted through trocar sleeves 78 and 84 are used to manipulate the opened catching device 70 into a predetermined position, for example, under ovaries OV1 and OV2, as depicted in FIG. 9B.

Membrane 72 remains in an at least partially opened configuration under ovaries OV1 and OV2 during a subsequent surgical operation in which the distal ends of laparoscopic instruments (not shown) are inserted into abdominal cavity AC through trocar sleeves 78 and 84. During the laparoscopic operation, as described hereinabove, catching device 70 functions to collect falling organic debris, e.g., tissue particles and fluid such as blood.

Figure 9C:
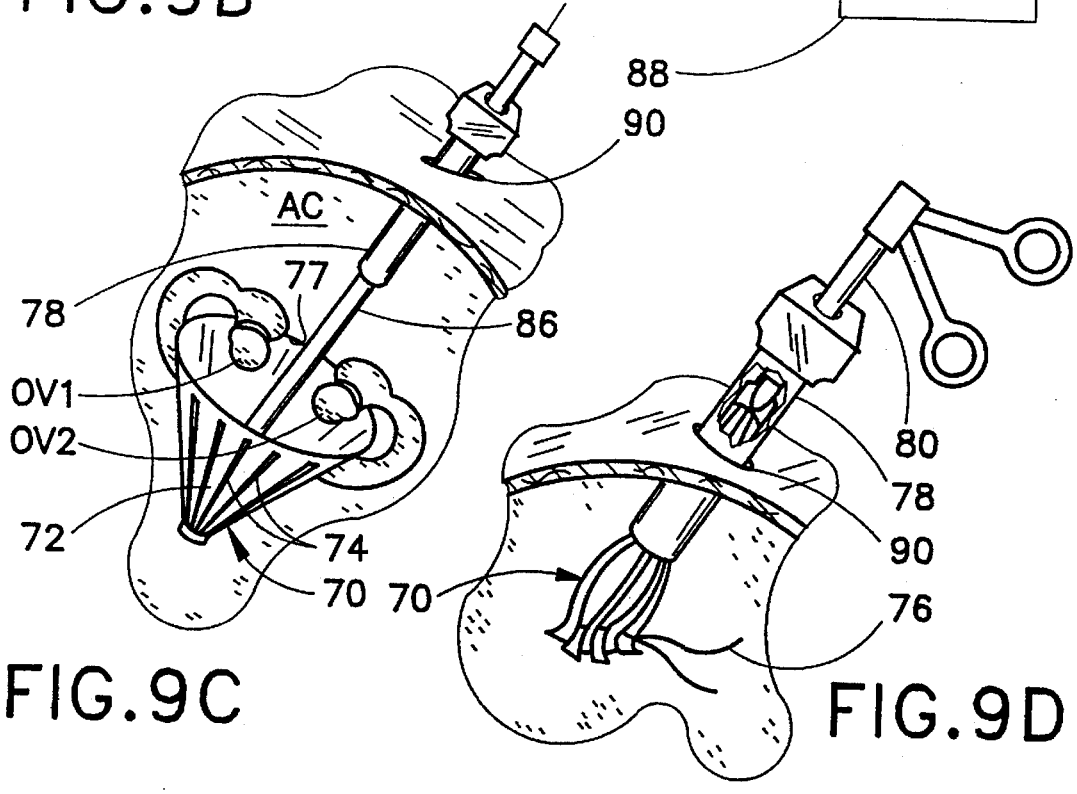

Upon completion of the laparoscopic operation, a distal end of a laparoscopic suction instrument 86 is inserted through trocar sleeve 78 (or 84), as shown in FIG. 9C. Upon subsequent insertion of the distal end of laparoscopic suction instrument 86 into catching device 70, a vacuum generated by a suction source 88 and conveyed by the suction instrument serves to remove the organic material and fluids collected by device 70.

Upon withdrawal of suction instrument 86, laparoscopic grasping instruments 80 and 82 are reinserted through sleeves 78 and 84 and manipulated to remove catching device 70 from its use location and to pull purse string 76 and thereby contract membrane mouth 77. Catching device 70 may then be pulled, mouth 77 first, through trocar sleeve 78 by laparoscopic grasping instrument 80. If a large piece of organic tissue, too large to be sucked away via suction instrument 86, is retained inside membrane 72, it may be necessary to remove trocar sleeve 78 from a perforation 90 in abdominal wall AW prior to the removal of catching device 70 through perforation 90.

Figure 9D:
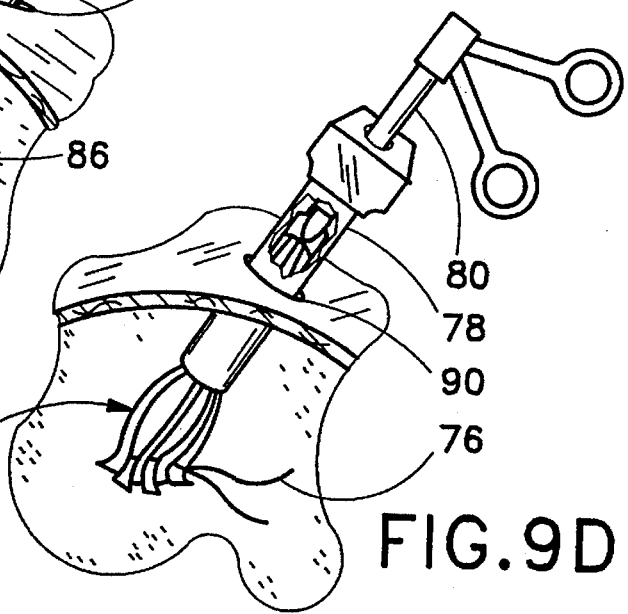

In the event that purse string 76 is omitted or is not used to close membrane 72, catching device 70 is inverted so that mouth 77 faces away from trocar sleeve 78 (or 84). As illustrated in FIG. 9D, grasping instrument 80 is used to pull catching device 70 backwards through trocar sleeve 78 and/or through perforation 90. Such a procedure assumes that organic material, particular fluids, have been removed from the inside of membrane 72 prior to the inversion of catching device 70.

It is to be noted that catching device 70 may be provided at mouth 77 with an oval or circular spring member (not shown) in the manner discussed hereinabove with reference to FIG. 7. The oval spring member has a memory so as to return to an oval or circular configuration upon the relaxation of externally applied forces.

Although the invention has been described in terms of particular embodiments and applications, one of ordinary skill in the art, in light of this teaching, can generate additional embodiments and modifications without departing from the spirit of or exceeding the scope of the claimed invention. For example, membrane 72 may be sealed along mouth 77 upon the termination of a laparoscopic operation, by the application of heat (e.g., via a cautery instrument) and/or pressure (via a laparoscopic clamping instrument). In addition, a disinfectant may be applied to the inner surface of membrane 72. If the disinfectant is applied as a liquid, it is sucked out of the catching device 70 by suction instrument 86.

Accordingly, it is to be understood that the drawings and descriptions herein are profferred by way of example to facilitate comprehension of the invention and should not be construed to limit the scope thereof.

What is claimed is:

1. A method for use in pelvic or peritoneal surgery, comprising the steps of:
   providing a trocar sleeve and a funnel shaped membrane;
   positioning said sleeve in the abdominal wall of the patient so that a distal end portion of said sleeve extends through a perforation into the abdominal cavity;

inserting said membrane in a closed configuration through said sleeve into the abdominal cavity of the patient;

upon emergence of said membrane into the abdominal cavity, spreading said membrane from said closed configuration to an opened configuration;

positioning the opened membrane and an internal organ of the patient relative to one another so that said organ, while attached to the patient, is disposed essentially vertically above said opened membrane;

operating on said organ while said organ is disposed above said opened membrane and is attached to the patient, whereby tissue particles and fluid escaping said organ during the operation fall into said opened membrane; and upon termination of said step of operating, removing said membrane and collected tissue particles and fluid from said abdominal cavity.

2. The method defined in claim 1 wherein said step of removing includes the steps of:

providing a laparoscopic suction instrument;

inserting a distal end portion of said suction instrument into the abdominal cavity of the patient; and operating said suction instrument to suck collected tissue particles and fluid from said opened membrane.

3. The method defined in claim 2 wherein said membrane has a mouth and a tapered side opposite said mouth, said step of removing further includes the step of drawing said membrane, said tapered side first, through said perforation in the abdominal wall of the patient.

4. The method defined in claim 3 wherein said step of removing further including the step of closing said mouth prior to said step of drawing.

5. The method defined in claim 4 wherein said step of closing includes the step of drawing closed a purse string about said mouth.

6. The method defined in claim 1, further comprising the steps of:

dropping a large mass of organic tissues into said opened membrane during said step of operating;

closing said membrane about said mass; and withdrawing a mass with said sleeve through a perforation in the abdominal wall of the patient.

7. The method defined in claim 6 wherein said membrane has a mouth, said step of closing includes the step of drawing closed a purse string about said mouth.

8. The method defined in claim 1, further comprising the step of capturing tissue samples fallen into said opened membrane during said step of operating.

9. The method defined in claim 8 wherein said membrane has a proximal end, said step of capturing including the step of suctioning the tissue samples from said proximal end of said membrane.

10. The method defined in claim 1 wherein said step of spreading includes the step of automatically opening said membrane from said closed configuration.

11. The method defined in claim 1 wherein said step of operating includes the step of inserting a distal end portion of at least one laparoscopic operating instrument into the peritoneal cavity through an additional trocar sleeve positioned in the abdominal wall of the patient.

12. The method defined in claim 2 wherein said membrane has a mouth and a tapered side opposite said mouth, said step of removing further including the step of drawing said membrane, said tapered side first, through another perforation in the abdominal wall of the patient.

13. The method defined in claim 1, further comprising the steps of:

dropping a large mass of organic tissues into said opened membrane during the step of operating;

closing said membrane about said mass; and withdrawing said mass with said sleeve through another perforation in the abdominal wall of the patient.

14. A method for use in pelvic or peritoneal surgery on a female patient, comprising the steps of:

providing a trocar sleeve and a funnel shaped membrane;

positioning said sleeve in an abdominal wall of the patient so that a distal end portion of said sleeve extends into the abdominal cavity;

inserting said membrane in a closed configuration through said sleeve into the abdominal cavity of the patient;

upon emergence of said membrane into the abdominal cavity, spreading said membrane from said closed configuration to an opened configuration;

positioning the opened membrane and an ovary of the patient relative to one another so that said ovary, while attached to the patient, is disposed vertically above said opened membrane;

operating on said ovary while said ovary is disposed above said opened membrane and is attached to the patient;

collecting tissue particles and fluid escaping said ovary during the operation in the opened membrane; and upon termination of said step of operating, removing, from said abdominal cavity, said membrane and tissue particles and fluid collected therein during the operation.

15. A method for use in pelvic or peritoneal surgery, comprising the steps of:

providing a trocar sleeve, a funnel shaped membrane, and a laparoscopic grasping instrument;

positioning said sleeve in the abdominal wall of the patient so that a distal end portion of said sleeve extends into the abdominal cavity;

inserting said membrane in a closed configuration through said sleeve into the abdominal cavity of the patient;

upon emergence of said membrane into the abdominal cavity, spreading said membrane from said closed configuration to an opened configuration;

positioning the opened membrane and an internal organ of the patient relative to one another so that said organ, while attached to the patient, is disposed essentially vertically above said opened membrane;

operating on said organ while said organ is disposed above said opened membrane and is attached to the patient, whereby tissue particles and fluid escaping said organ during the operation fall into said opened membrane;

after inserting said membrane into the abdominal cavity, inserting a distal end portion of said grasping instrument into the abdominal cavity;

grasping said membrane with said grasping instrument; and subsequently withdrawing said membrane from the abdominal cavity with said grasping instrument.

16. The method defined in claim 15 wherein said grasping instrument is inserted after completion of said step of operating.

17. The method defined in claim 16, further comprising the steps of initially inserting the grasping instrument into the abdominal cavity prior to said step of operating, and subsequently removing said grasping instrument from the abdominal cavity prior to said step of operating.

18. The method defined in claim 17 wherein said step of spreading said membrane is performed at least in part by said grasping instrument.

19. The method defined in claim 17 wherein said step of positioning said membrane is performed at least in part by said grasping instrument.

20. The method defined in claim 15, further comprising removing collected tissue particles and fluid from the abdominal cavity prior to withdrawing said membrane from the abdominal cavity.

* * * * *